US006929004B1

(12) United States Patent
Bonney et al.

(10) Patent No.: US 6,929,004 B1
(45) Date of Patent: Aug. 16, 2005

(54) MEDICAMENT CARRIER (75) Inventors: Stanley George Bonney, Ware (GB);
Michael Birsha Davies, Ware (GB);
James William Godfrey, Ware (GB);
Sylvia Maria Haglund, Edinburgh
(GB); Paul Kenneth Rand, Ware (GB)

(73) Assignee: SmithKline Beecham Corporation,
Philadelphia, PA (US)

( * ) Notice: Subject to any disclaimer, the term of this
patent is extended or adjusted under 35
U.S.C. 154(b) by 0 days.

(21) Appl. No.: 10/031,261

(22) PCT Filed: Apr. 19, 2000

(86) PCT No.: PCT/EP00/03518

§ 371 (c)(1),
(2), (4) Date: Jan. 10, 2002

(87) PCT Pub. No.: WO00/64779

PCT Pub. Date: Nov. 2, 2000

(30) Foreign Application Priority Data

Apr. 24, 1999 (GB) .................................... 9909357

(51) Int. Cl.[7] ............................................ A61M 15/00
(52) U.S. Cl. ............................. 128/203.15; 128/203.21
(58) Field of Search ................. 128/203.15, 203.21;
206/438, 494; 221/22, 25–27, 33, 38, 48,
221/70

(56) References Cited

U.S. PATENT DOCUMENTS

| 103,012 | A | * | 5/1870 | Button ........................ 206/225 |
|---|---|---|---|---|
| 776,649 | A | * | 12/1904 | Dumont et al. ............. 206/247 |
| 895,527 | A | * | 8/1908 | Williams .................. 206/459.5 |
| 1,192,859 | A | * | 8/1916 | Canfield ....................... 221/25 |
| 1,476,682 | A | * | 12/1923 | Beckmann .................. 128/894 |
| 1,490,529 | A | * | 4/1924 | Dittgen ....................... 206/258 |
| 2,197,845 | A | * | 4/1940 | Ward .......................... 206/309 |
| 2,298,451 | A | * | 10/1942 | Balthasar .................... 493/345 |
| 2,399,000 | A | * | 4/1946 | Carroll ........................ 222/210 |
| 2,465,879 | A | * | 3/1949 | Hornung ....................... 221/72 |
| 2,598,823 | A | * | 6/1952 | O'Grady ..................... 422/125 |
| 2,889,958 | A | * | 6/1959 | Ekenstam et al. ............ 221/25 |
| 2,968,396 | A | | 1/1961 | Pratt |
| 2,989,212 | A | * | 6/1961 | Ekenstam et al. ............ 221/25 |
| 3,039,652 | A | * | 6/1962 | Ekenstam et al. ............ 221/25 |
| 3,107,782 | A | * | 10/1963 | Jaroff et al. ................ 206/362 |
| 3,301,392 | A | * | 1/1967 | Regan, Jr. ................... 206/363 |
| 3,338,400 | A | * | 8/1967 | Edgworth et al. .......... 206/363 |
| 3,342,326 | A | * | 9/1967 | Zackheim ................... 222/211 |
| 3,482,733 | A | * | 12/1969 | Groves ......................... 221/25 |
| 3,692,176 | A | * | 9/1972 | Templeton et al. ......... 206/460 |
| 3,698,549 | A | | 10/1972 | Glassman |

(Continued)

FOREIGN PATENT DOCUMENTS

EP 0 101 298 A 2/1984

(Continued)

Primary Examiner—Aaron J. Lewis
(74) Attorney, Agent, or Firm—James P. Riek (57) ABSTRACT There is provided a carrier comprising a sheet (10) having a first portion and a second portion; a retainer (20) in said first portion for containment of product; a fold in said second portion such that the second portion is foldable towards said retainer to form a cover therefor; and a join between said cover and the retainer. The carrier is suitable for the containment of a range of different products, particularly medicaments.

83 Claims, 7 Drawing Sheets

U.S. PATENT DOCUMENTS

| | | | | |
|---|---|---|---|---|
| 3,856,142 | A | * | 12/1974 | Vessalo ...................... 206/530 |
| 3,967,761 | A | * | 7/1976 | Melton et al. ............... 222/635 |
| 4,373,631 | A | * | 2/1983 | Friese et al. ................ 206/438 |
| 4,428,709 | A | * | 1/1984 | Peters ........................ 414/412 |
| 4,444,310 | A | * | 4/1984 | Odell .......................... 206/366 |
| 4,474,349 | A | * | 10/1984 | Loeckle ...................... 244/136 |
| 4,762,124 | A | * | 8/1988 | Kerch et al. ................ 604/307 |
| 4,781,696 | A | * | 11/1988 | Moulding et al. ........... 604/189 |
| 4,884,719 | A | * | 12/1989 | Levine et al. ................. 221/25 |
| 4,913,311 | A | * | 4/1990 | Garcia .......................... 221/22 |
| 5,011,017 | A | * | 4/1991 | Giesen ....................... 206/494 |
| 5,239,991 | A | * | 8/1993 | Chawla et al. ......... 128/203.15 |
| 5,411,168 | A | * | 5/1995 | Mertens et al. ................ 221/22 |
| 5,511,689 | A | * | 4/1996 | Frank ........................... 221/73 |
| 5,533,505 | A | * | 7/1996 | Kallstrand et al. ..... 128/203.15 |
| 5,590,645 | A | | 1/1997 | Davies |
| 5,660,169 | A | * | 8/1997 | Kallstrand et al. ..... 128/203.15 |
| 6,059,112 | A | * | 5/2000 | Dykstra et al. ............. 206/438 |
| 6,085,936 | A | * | 7/2000 | Friar et al. .................... 221/25 |
| 6,286,507 | B1 | * | 9/2001 | Jahnsson ............... 128/203.15 |

FOREIGN PATENT DOCUMENTS

| | | |
|---|---|---|
| FR | 850 597 A | 12/1939 |
| WO | WO 88 10219 A | 12/1988 |

* cited by examiner

FIG. 3b  PULL

MEDICAMENT CARRIER

This application is a U.S. National Phase filing, filed under 35 USC 371 of PCT Patent Application PCT/EP00/03518 filed 19 Apr. 2000 with priority application with priority to GB9909357.7 filed 24 Apr. 1999 in the United Kingdom.

The present invention relates to a carrier for containment of a product. In particular, it relates to a medicament carrier for incorporation into an inhalation device to enable administration of medicament to a patient.

Individual carriers or blister packs are widely used across many different industries to package, present and deliver products to customers, users and patients. Thus, for instance, blister packs containing unit quantities of food, toiletries, cosmetics, electrical and photographic products are commonly sold in supermarkets. These packs are generally designed to provide a clean, durable, moisture-free environment to protect and present products while at the same time offering easy accessibility for the consumer at low cost. Blister packs are particularly suitable for use within the pharmaceutical and health care industries.

Inhalation devices are known for use with blister packs in which the medicament is held in powder form in the blisters thereof. Such packs are typically comprised of two separate entities, one of which is suitably formed to define the medicament retainer and the other is hermetically sealed to the first to form the medicament carrier. It is an object of the present invention to provide a medicament carrier wherein the carrier comprises a single sheet or elongate strip thus providing significant advantages over the prior art in that the strip is straightforward to manufacture, providing both ease of use and reduction in manufacturing costs.

Known drug delivery systems including blister packs generally include a puncturing member, which punctures each blister in turn thus enabling the medicament to be inhaled therefrom. Generally release of the medicament dose is by puncture or rupture of the second entity. Such packs suffer from the disadvantage that they may be difficult to use, particularly as the dose releasing means may comprise one or more elongate members, such as cords or tapes, which are separately attached to films used to seal the medicament retainers. The present invention in embodiments provides advantages over such packs in that it is especially useful for the elderly and infirm since the free end of the strip is readily identifiable and simple to grasp, without the added complication of numerous cords or tapes which act as a separate release mechanism.

It will also be seen that in several embodiments of the present invention the free end of the sheet or strip is peeled back automatically by virtue of a releasing means incorporated into the inhalation device, hence avoiding the need to grasp the strip manually. Such a feature further enhances the ease of use of the inhalation device since minimum force is required by the user to peel back the medicament retainer.

It is also an object of the present invention to provide a medicament carrier for use in combination with an inhalation device, wherein the design of the inhalation device has the potential, if desired, to handle a medicament carrier having a large number of discrete unit doses without the device becoming unacceptably large. Thus, although a single use inhaler is referred to it the drawings/illustrations, it is possible that such an inhaler may be easily adapted to accommodate a multi-dose medicament container.

It is a further object of the present invention to provide a carrier for a wide range of different product types, comprising a single sheet or elongate strip, which is easy to use and of low manufacturing cost.

According to one aspect of the present invention there is provided a carrier comprising a sheet having a first portion for containment of product, said retainer comprising a pocket or a hole therein a fold in the second portion such that the second portion is foldable towards the retainer to form a cover therefor; and a join between the cover and the retainer.

Preferably the sheet comprises an elongate strip. More preferably the hole additionally comprises a seal applied therefo.

In another aspect of the invention there is provided a carrier comprising a plurality of retainers in the first portion, wherein the second portion is foldable towards the plurality of retainers to form a cover therefor; and a join between the cover and the plurality of retainers.

In a further aspect of the invention there is provided a carrier additionally comprising a fold in the first portion such that the first portion is foldable towards the retainer to form a base therefor; and a join between the base and the retainer.

In one aspect of the invention there is provided a carrier additionally comprising an inert support within the retainer for bearing product thereon. Typically this support comprises a grid, mesh, sponge or disc to which product is entrapped, absorbed or adsorbed.

In another aspect of the invention there is provided a carrier comprising a second fold in the second portion to form a pull release tab.

Preferably, the pull release tab is shaped for ease of grip.

Preferably, the pull release tab has a looped end enabling it to be connected to a release mechanism incorporated within a device, such as an inhalation device, or for receipt of finger in manual release.

Preferably, the pull release tab has at least one perforation therein allowing it to be easily grasped by the user or otherwise allowing it to be connected to a release mechanism incorporated within a device such as an inhalation device.

In another aspect of the invention there is provided a carrier in multi-unit form comprising a series arrangement of a plurality of carriers as described above.

Preferably, each of the plurality of carriers is connected together.

More preferably, each of the plurality of carriers is formable from the same sheet or elongate strip.

In one aspect, the sheet or elongate strip has a point of weakness between each carrier in the series arrangement, thereby enabling separation of individual carriers from the sheet or elongate strip.

Preferably, the sheet or elongate strip is flexible to enable it to be formed for example, into a spiral, helical or zig-zag shape for incorporation into a suitable device, such as an inhalation device. More preferably, the sheet or elongate strip comprises material selected from the group consisting of metal foil, an organic polymeric material and paper. Most preferably, the carrier comprises a laminate.

Preferably, the join is formable by a joining method selected from the group consisting of heat, laser, radio frequency, adhesive, staple, stamp, pressure and ultrasonic sealing.

Preferably, the join is peelable to enable peelable access to the retainer.

Preferably, the retainer consists of a pocket or hole.

In a further aspect, there is provided a carrier comprising a medicament therein. Preferably the medicament is in dry powder, tablet, liquid, paste, cream or capsular form. More preferably the medicament is selected from the group consisting of albuterol, salmeterol, ipratropium bromide, fluticasone propionate and beclomethasone dipropionate and salts or solvates thereof and any mixtures thereof.

According to another aspect of the present invention, there is provided an inhalation device comprising a housing in combination with a medicament carrier as described above. Preferably the housing includes a holder for receipt of the retainer of the carrier. More preferably the inhalation comprises a pull release tab and the pull release tab protrudes from the housing.

Preferably the inhalation device comprises a release mechanism and the pull release tab connects to the release mechanism. More preferably, the release mechanism is separable from the housing of the inhalation device.

According to another aspect of the present invention, there is provided a method of making a carrier comprising forming a retainer, comprising a pocket or hole therein, in a first portion of a sheet or elongate strip; filling the retainer with product; folding a second portion of the sheet or elongate strip towards the retainer to form a cover therefor; and forming a join between the cover and the retainer.

In one aspect, there is provided a method comprising forming a plurality of retainers in a portion of a sheet or elongate strip; filling the plurality of retainers with product; folding a second portion of the sheet or elongate strip towards the plurality of retainers to form a cover therefor; and forming a join between the cover and the plurality of retainers.

In an other aspect, there is provided a method of making a carrier as described above additionally comprising a fold in the first portion such that the first portion is foldable towards the retainer to form a base therefor; and a join between the base and the retainer.

Preferably there is provided a method of making a carrier in multi-unit form comprising successive iterations of the method described above to form a series arrangement of a plurality of carriers.

According to another aspect of the present invention, there is provided a method of opening a carrier as described above comprising pulling the pull release tab in order to enable access to the retainer.

In a further aspect of the present invention, there is provided the use of a carrier, as described above, for dispensing medicament.

In a preferred aspect, the medicament is used in the treatment of respiratory disorders. More preferably the medicament is used in the treatment of asthma. Most preferably the medicament is salbutamol or albuterol.

In one aspect, there is provided a carrier comprising an electronic component therein. Preferably the electronic component is selected from the group consisting of semiconductor, integrated circuit chip, fuse and battery.

In another aspect, there is provided a carrier comprising a food therein. Preferably the food is selected from the group consisting of meat, mycoprotein, milk, cheese, flour, pasta, rice, oil, sugar, confectionery, vegetable, herbal, snack, convenience and fruit foodstuffs.

In a further aspect, there is provided a carrier comprising a beverage therein. Preferably the beverage is selected from the group consisting of water, milk, coffee, cocoa, tea, fruit, carbonated and alcoholic drinks.

In one aspect, there is provided a carrier comprising a toiletry therein. Preferably the toiletry is selected from the group consisting of toothpaste, soap, mouthwash, shampoo, skin and face cream.

In another aspect, there is provided a carrier comprising a cleanser therein. Preferably the cleanser is selected from the group consisting of soap, detergent, enzymic preparation and organic solvent.

In a further aspect, there is provided a carrier comprising a disinfectant therein. Preferably the disinfectant is selected from the group consisting of sterilant, antiseptic and bleach.

In another aspect, there is provided a carrier comprising a light-sensitive material therein. Preferably the light-sensitive material comprises a photographic film.

In yet another aspect, there is provided a carrier comprising a marking material therein. Preferably the marking material is selected from the group consisting of toner, ink, dye, pigment, acid and alkali.

In one aspect, there is provided a carrier comprising a covering material therein. Preferably the covering material is selected from the group consisting of paint, pigment, dye, corrosion inhibitor, electrical conductor, electrical insulator and static inhibitor.

In a further aspect, there is provided a carrier comprising a toy therein. Preferably the toy is selected from the group consisting of model, figure, doll, animal, jigsaw and game.

In another aspect, there is provided a carrier comprising haberdashery therein. Preferably the haberdashery is selected from the group consisting of button, bobbin, needle, pin, eye, hook and fastener.

In one aspect, there is provided a carrier comprising a tool therein. Preferably the tool comprises a domestic tool. More preferably, the domestic tool is selected from the group consisting of can opener, bottle opener, ring-pull opener, scissors, knife, fork and spoon.

Optionally the tool comprises a home maintenance tool. Preferably the home maintenance tool is selected from the group consisting of nail, screw, pin, wire, screwdriver, knife, brush, spanner, ruler and marker.

In another aspect, there is provided a carrier comprising stationery therein. Preferably the stationery is selected from the group consisting of pencil, pen, ruler, crayon, eraser, marker, stencil, protractor, compass and paper.

In a further aspect, there is provided a carrier comprising an adhesive therein. Preferably the adhesive bonds materials selected from the group consisting of paper, plastic, wood, rubber, glass and metal.

In one aspect, there is provided a carrier comprising an agrochemical therein. Preferably the agrochemical is selected from the group consisting of herbicide, insecticide, fungicide, rodentocide, nematocide, acaracide and plant growth regulator.

In another aspect, there is provided a carrier comprising a plant seed therein. Preferably the seed is derived from plants selected from the group consisting of monocotyledonous and dicotyledonous plants.

In a further aspect, there is provided a carrier comprising a contraceptive therein. Preferably the contraceptive is either a contraceptive device or a contraceptive drug. Preferably the contraceptive device is selected from the group consisting of condom, diaphragm, sponge and coil. Preferably the contraceptive drug is selected from the group consisting of spermacide, estrogen, ethinyl estradiol, progesterone, levonorgestrel and norgestrel.

In one aspect, there is provided a carrier comprising a medical instrument therein. Preferably the medical instrument is selected from the group consisting of scalpel, thermometer and syringe.

In another aspect, there is provided a carrier comprising laboratory equipment therein. Preferably the equipment is selected from the group consisting of dispenser tip, microbial filter, filter paper, aseptic container, petri-plate, vial, test tube, tissue-culture vessel and pipette.

In a further aspect, there is provided a carrier comprising a catemenial product therein. Preferably the catemenial product comprises a tampon.

In another aspect, there is provided a carrier comprising nicotine therein.

Preferred embodiments of the medicament carrier according to the present invention will now be described with reference to the accompanying drawings in which.

Figure 1A:
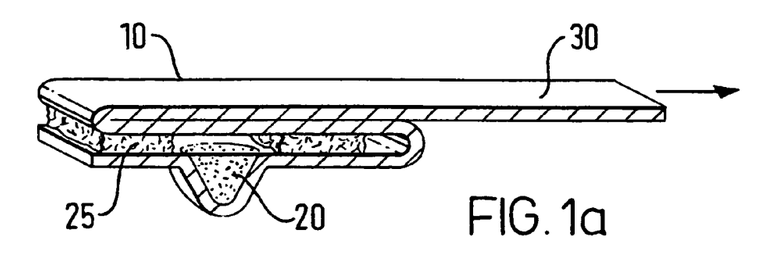
FIG. 1a is a cross-sectional perspective sideview of a first medicament carrier in accordance with the present invention in the closed configuration.

FIG. 1a shows a medicament carrier in the closed configuration comprising an elongate strip 10, whose first portion contains a blister 20 suitable for containing a powdered medicament. A second portion of the elongate strip is folded over once to form a cover for the blister 20 and folded a second time to define a pull release tab 30. The contents of the blister 20 are exposed by pulling the pull release tab 30 in a horizontal direction relative to the medicament retainer, either manually or by a release mechanism, to break the seal 25 around the periphery of the blister 20, so that the medicament carrier is then in the open configuration as shown in FIG. 1b.

Figure 1B:
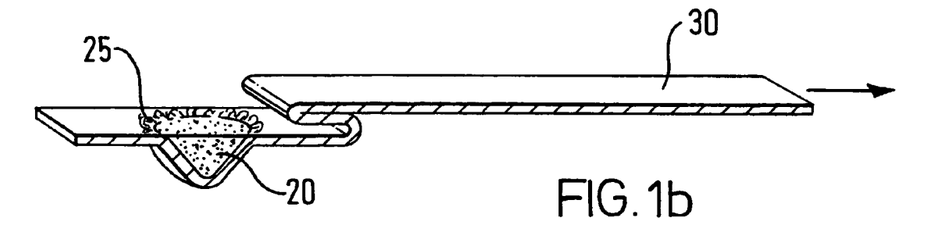
FIG. 1b is a cross-sectional perspective sideview of the first medicament carrier in accordance with the present invention in the open configuration.

FIG. 1b shows the medicament carrier of FIG. 1a in the open configuration wherein the pull release tab 30 has been sufficiently peeled in order to break seal 25 around the periphery of the blister 20 thereby removing the cover portion and exposing the medicament contained therein.

Figure 1C:
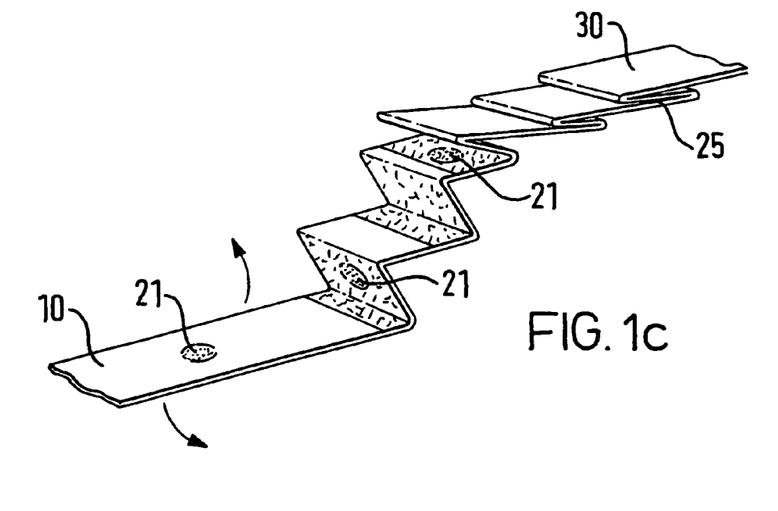
FIG. 1c is a perspective sideview of a second medicament carrier in accordance with the present invention in the open and closed configuration.

FIG. 1c shows a second embodiment of a medicament carrier according to the present invention. Elongate strip 10 has a series of retainers 21 each comprising a mesh which itself comprises a plurality of holes for containment of medicament. The first portion of elongate strip 10 is folded toward mesh 21 to form a base therefor, while the second portion is folded (in the direction shown by the arrows) to form a cover for mesh 21. On folding, seals 25 are formed around the periphery of mesh 21 between the cover (not shown) and base sheets. Medicament may be released from mesh 21 by pulling on tab 30 to break seal 25. The mesh 21 may in embodiments be substituted by a pocket for containment of medicament.

Figure 1D:
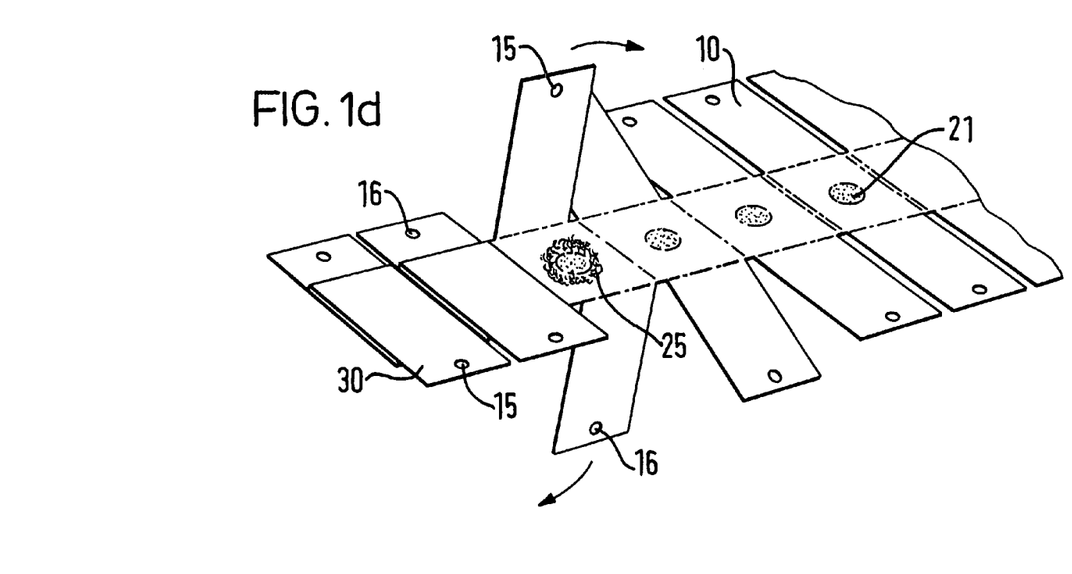
FIG. 1d is a perspective sideview of a third medicament carrier in accordance with the present invention in the open and closed configuration.

FIG. 1d shows a medicament carrier comprising a plurality of mesh retainers 21 in the open and closed configuration. The first portion of elongate strip 10 is folded toward retainer 21 to form a cover sheet while the second portion is folded in the opposite direction to form a base (as shown by the arrows). Seals 25 are formed around retainer 21 between the cover and base sheets. A hole 16 in the base sheet secures the medicament carrier within an inhalation device (not shown) while corresponding hole 15 engages an opening mechanism in the device. The medicament carrier is opened by gripping tab 30 directly, or by engaging hole 30, and pulling in an anti-clockwise manner.

Figure 2:
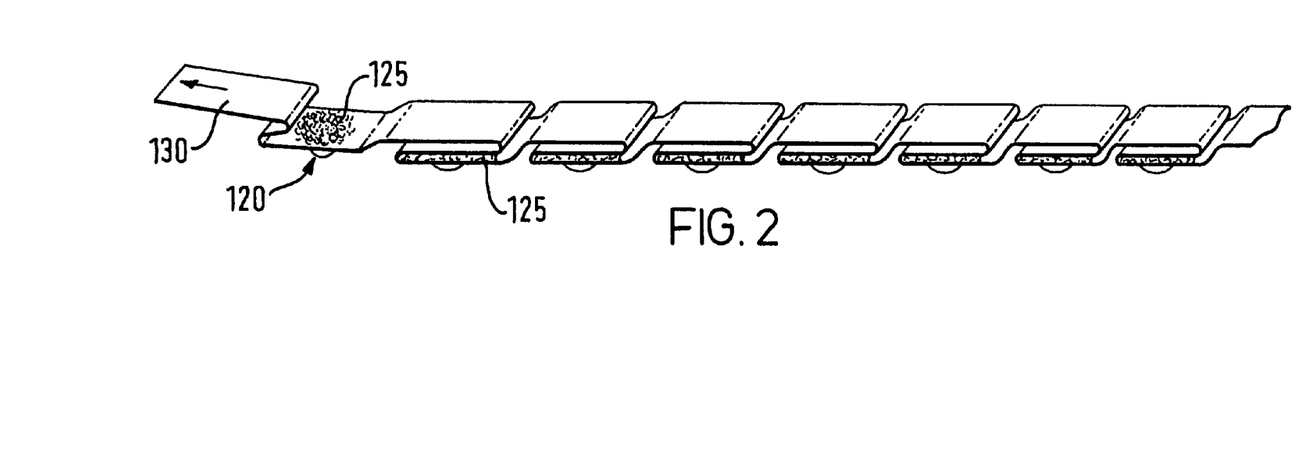
FIG. 2 is a perspective sideview of a fourth medicament carrier in a multi-dose form.

FIG. 2 shows a combination of FIGS. 1a and 1b in both the open and closed configurations in which the medicament carrier is in a multi-dose form. The multi-dose medicament carrier is formed from an elongate strip incorporating a number of first portions each containing a blister 120. A corresponding second portion is folded over once as described above in order to define a cover for said blister 120 and folded a second time to form a pull release tab 130 with which to break the seal 125 and expose the medicament contained within the blister.

Figure 3A:
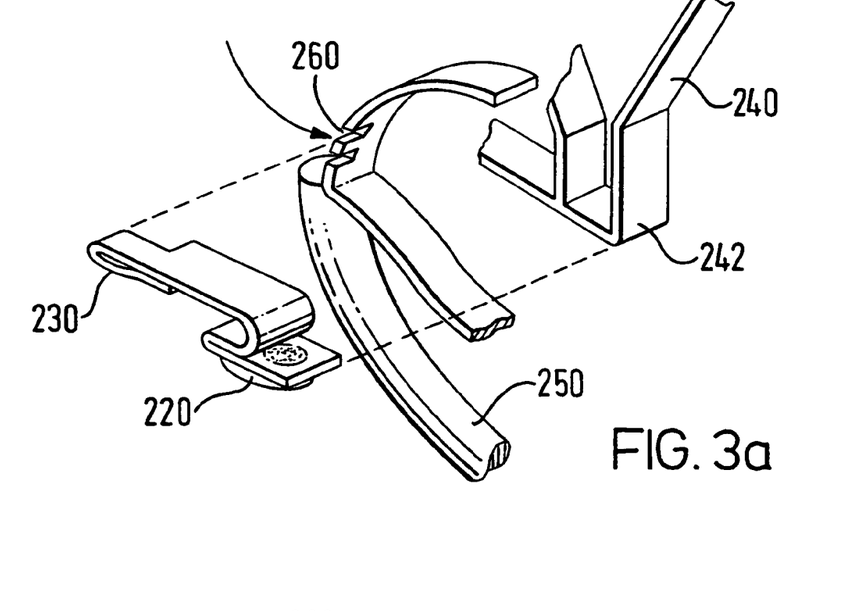
FIG. 3a is a perspective sideview of the insert of an inhalation device incorporating a medicament carrier, which is a variation of that shown in FIG. 1.

FIG. 3a shows the insert of a first inhalation device designed to accommodate the medicament carrier of the present invention. The insert comprises a separate housing 240 and a flexible ring 250 which slots into said housing. The ring 250 has at least one notch 260 at a suitable point on the circumference. The blister 220 (shown in the open configuration for exemplification only) sits in the closed configuration in support 242 within the inhalation device and the looped pull release tab 230 engages with the notch 260 to form a release mechanism for opening the cover of the blister. Actuation of the release mechanism is achieved by the user gripping the ring and pulling it in a downward motion, whereby the pull release tab 230 is automatically peeled backwards to expose the contents of the blister 220.

Figure 3B:
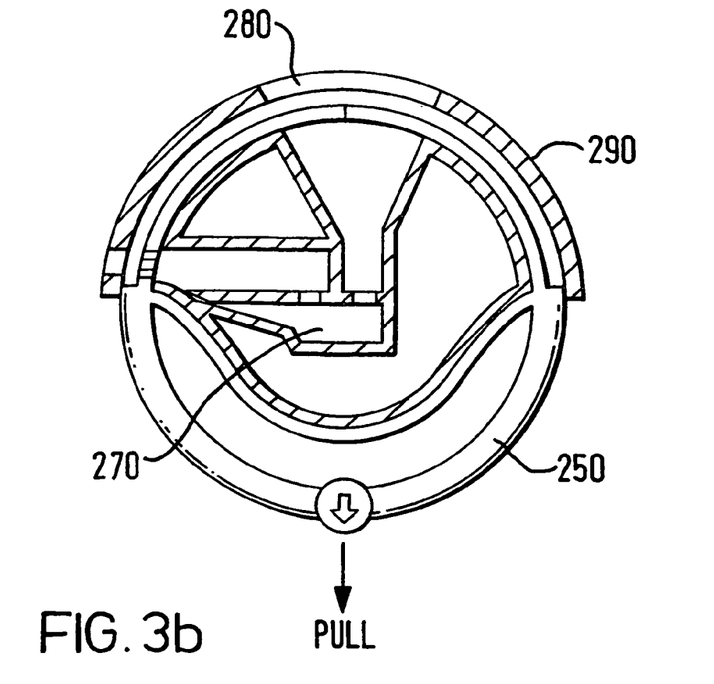
FIG. 3b is a cross-sectional front view of an inhalation device incorporating a medicament carrier, which is a variation of that shown in FIG. 1, wherein the mouthpiece is in the closed configuration.
Figure 3C:
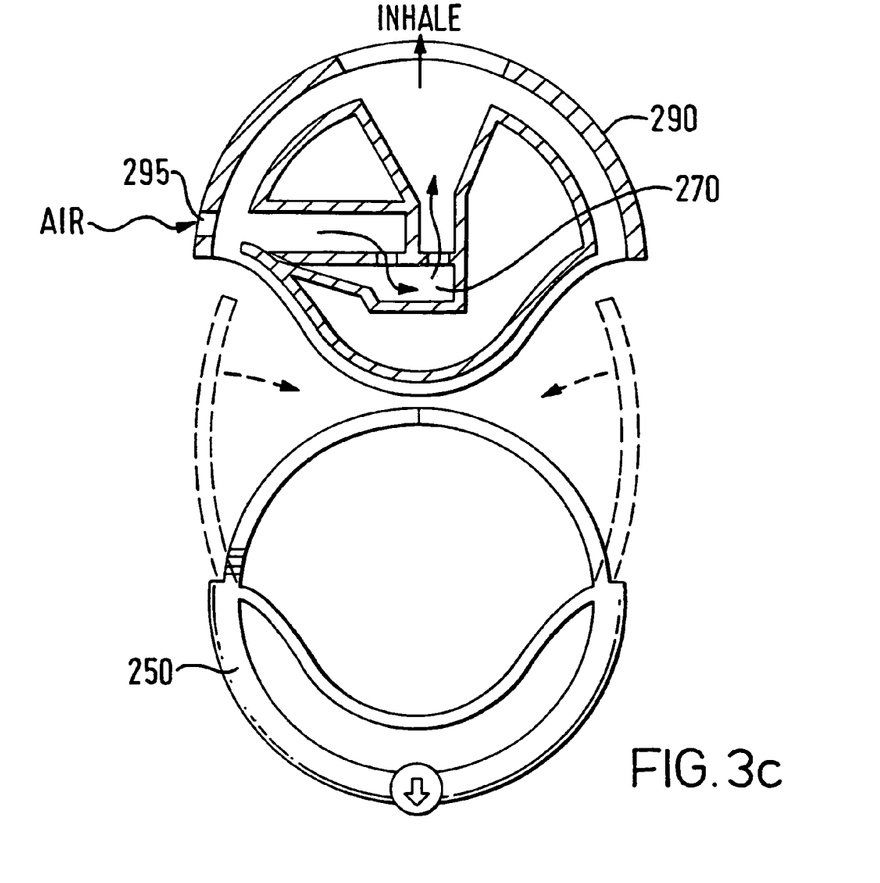
FIG. 3c is a cross-sectional front view of the inhalation device of FIG. 3b, wherein the carrier is in the open configuration.

FIGS. 3b and 3c show a first inhalation device comprising the insert described in FIG. 3a in the open and closed positions respectively. The medicament carrier of the present invention is housed in a recess 270 and connected to the ring 250 by the pull release tab 230 as described in FIG. 3a above. In the storage position (FIG. 3b) the circumference of the ring 250 seals the mouthpiece 280 and actuation of the device from this position to the in-use position (FIG. 3c) is achieved by a two-handed operation. In practice, this may be achieved by holding the body 290 of the device between thumb and forefinger and pulling the ring 250 in a downward motion as described in FIG. 3a. It will be seen that this action causes the pull release tab 230 to be peeled backwards and the contents of the blister 220 to be exposed. Complete removal of the ring 250 from the body of the device 290 uncovers both the mouthpiece 280 and an airway 295 at the side of the device, enabling the blister contents to be inhaled through the mouthpiece 280.

Figure 4A:
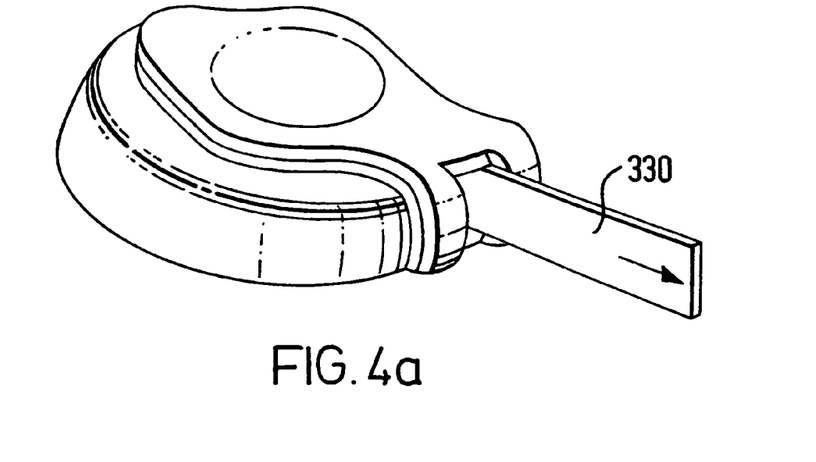
FIG. 4a is a perspective view of an inhalation device comprising a medicament carrier in accord with the present invention.
Figure 4B:
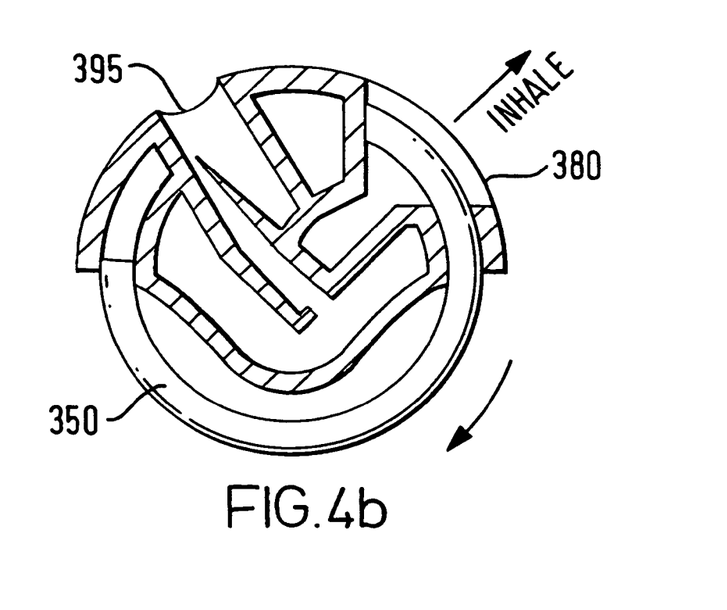
FIG. 4b is a cross-sectional front view of the insert of an inhalation device incorporating a medicament carrier, which is a variation of that shown in FIG. 1, wherein the mouthpiece is in the closed configuration.

FIGS. 4a and 4b show a second inhalation device comprising a similar insert to that described in FIG. 3a. FIG. 4a shows an inhalation device wherein the pull release tab 330 protrudes from the housing in order to be freely pulled by the patient. Actuation of the device is similar to that of the device in FIGS. 3b and 3c. This is achieved by pulling the pull release tab 330 as before (FIG. 4a) and rotating a rigid ring 350 (FIG. 4b) in order to uncover the mouthpiece 380 and airway 395 to allow the contents of the blister to be exposed.

Figure 5A:
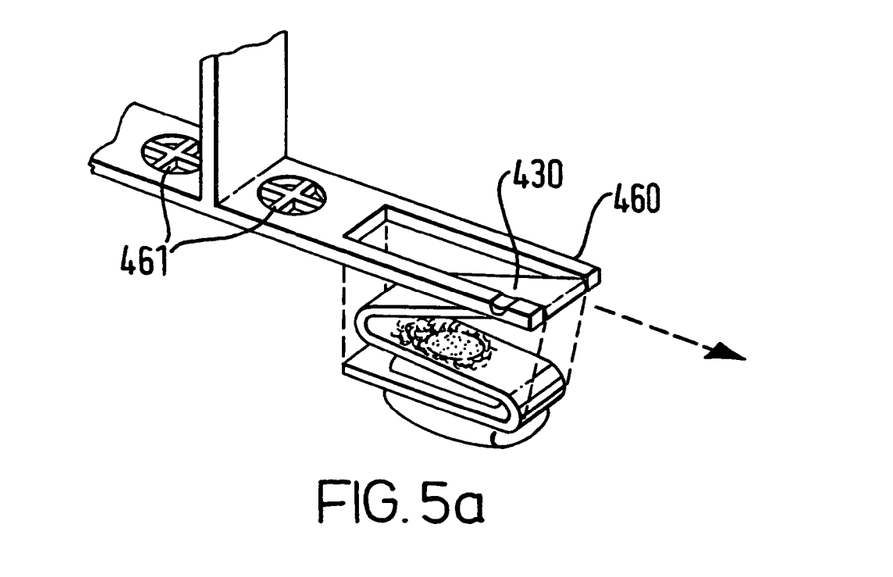
FIG. 5a is a perspective sideview of part of the insert of an inhalation device incorporating a medicament carrier, which is a variation of that shown in FIG. 1.

FIG. 5a shows part of the insert of an inhalation device encompassing a medicament carrier which is a variation of that shown in FIG. 1a wherein the looped pull release tab 430 is attached to a notch 460 in the insert to provide a release mechanism. Ports 461 enable air flow through the inhalation device when in use.

Figure 5B:
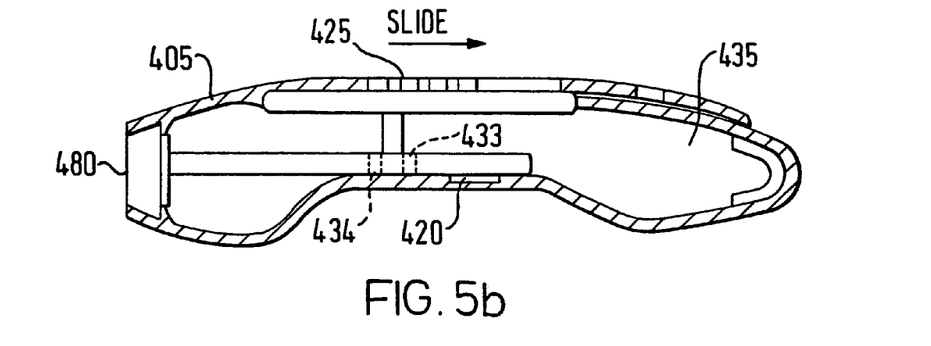
FIG. 5b is a cross-sectional sideview of an inhalation device incorporating a medicament carrier, which is a variation of that shown in FIG. 1, wherein the center is in the closed configuration.
Figure 5C:
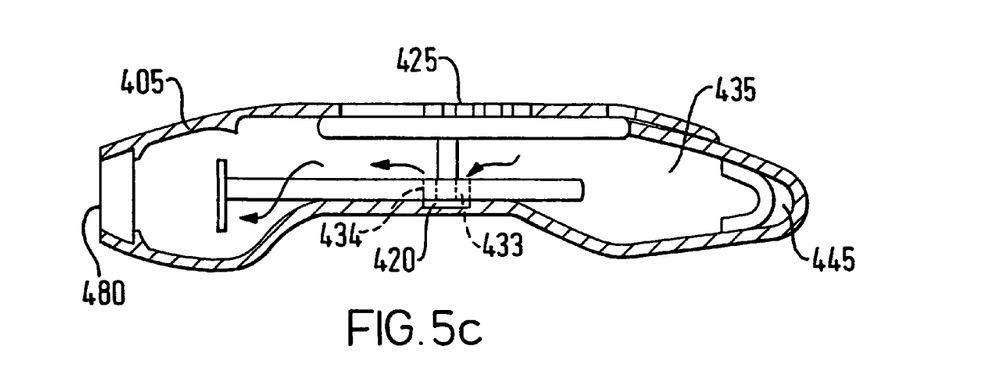
FIG. 5c is a cross-sectional sideview of the inhalation device of FIG. 5b, wherein the carrier is in the open configuration.

FIGS. 5b and 5c show a third inhalation device for use with the insert of FIG. 5a. The device comprises a tubular-shaped body 405 into which position 420 a blister is located when attached to an insert similar to that described in FIG. 5a. The inhalation device has a mouthpiece 480 and a slidably movable projection 425. In the storage position (FIG. 5b) the projection 425 is located close to the mouthpiece 480 so that both the mouthpiece and the airway 435 are covered. Actuation of the device from this position to the in-use position (FIG. 5c) is achieved by sliding the projection 425 translationally to the forward locked position, thereby pulling tab 430 and exposing medicament within blister 420 for release. On inhalation by the patient through the mouthpiece 480, air is drawn through airway 435 and then through passage 433 to the blister 420 wherein medicament is drawn out of the blister 420 through passage 434 and thence to the mouthpiece 480.

Figure 6A:
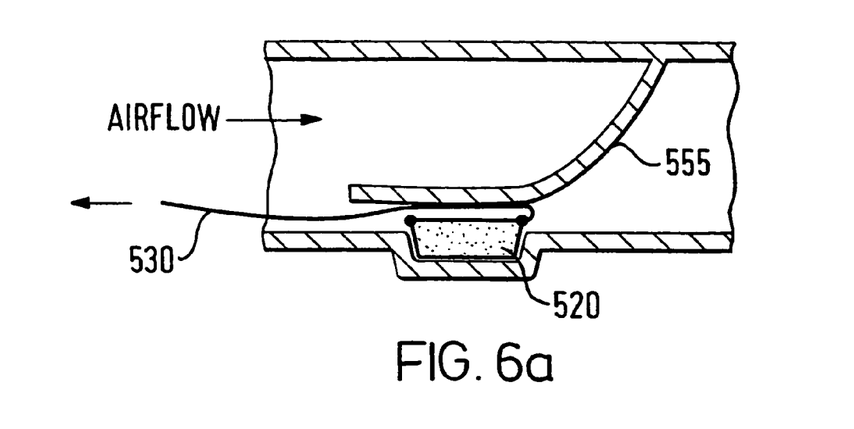
FIG. 6a is a cross-sectional sideview of the insert of an inhalation device incorporating a medicament carrier, which is a variation of that shown in FIG. 1, wherein the carrier is in the closed configuration.
Figure 6B:
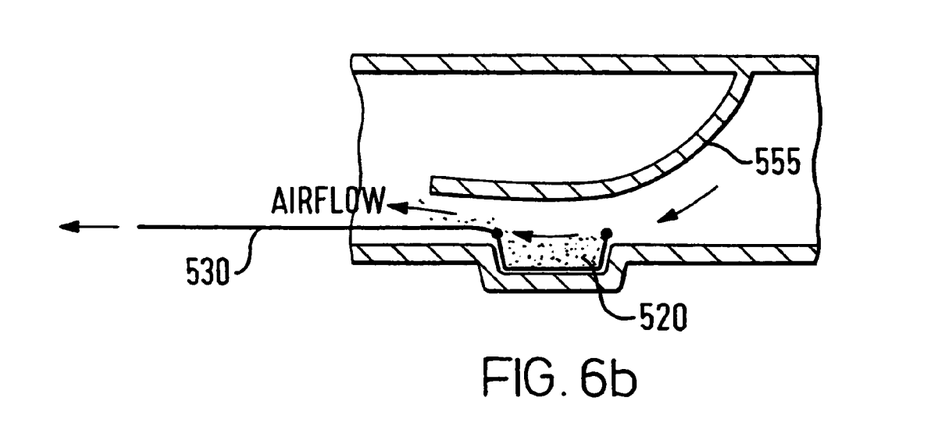
FIG. 6b is a cross-sectional sideview of the insert of FIG. 6a, wherein the carrier is in the open configuration.

FIGS. 6a and 6b show a fourth inhalation device incorporating a medicament carrier which is a variation of that in FIG. 1a in the open and closed positions, respectively. FIG. 6a shows that when the air flows towards the sealing flap 555 in the direction shown, the contact between the sealing flap 555 and the edge of the blister 520 is not broken. Such airflow would be created by exhalation. When the free end of the strip 530 is pulled to expose the contents of the blister 520 and the direction of airflow reversed by inhalation, as shown on FIG. 6b, then the sealing flap 555 is opened and the medicament present in the blister 520 is entrained in the airflow and carried through the device to be administered to the patient.

Standard methods of filling and sealing the medicament container may be used and form another aspect of the present invention. Such methods include entering a hollow, or a number of hollow, pin into a powder bed so that a defined quantity of powder is taken up into the or each pin. The pin, or number of pins, is then positioned above the individual medicament containers and the powder contained therein released by means of a piston. On removal of the pin, or pins, the medicament containers are sealed so that the powder is contained in a medicament container defined by the two portions of the elongate strip.

Suitable methods of sealing the medicament carrier include the use of adhesives, staples, stamps, pressure and welding methods selected from hot metal welding, radio frequency welding, laser welding and ultrasonic welding. Such sealing techniques may be used to form a suitable join around the periphery of the retainer which is capable of being peeled away by the patient or by a suitable release mechanism in a controlled manner when in use. The release mechanism may be designed to confer a mechanical advantage, thereby reducing the operating force required to break the seal.

Although not directly relevant to the present invention, it should be noted that medicaments suitable for administration by an inhalation device using the present invention are any drug particles suitable for delivery to the bronchial or alveolar region of the lung which have an aerodynamic diameter of less than 10 micrometers. Larger particles may be used if delivery to other portions of the respiratory tract is desired, such as the mouth or throat. Such medicaments may be selected from a wide range of powdered medicaments and may be in amorphous or crystalline form and may have been comminuted, e.g. ground, and, if necessary, classified and sieved, e.g. on an air jet sieve, to obtain a suitable size or may have been made by direct crystallisation to the desired size.

The medicament carrier herein is suitable for containing medicament, such as those for the treatment of ulcers, e.g., omeprazole, lansoprazole, lipid levels, e.g., simvastatin, atorvastatin, hypertension, e.g., amiodipine, depression, e.g. fluozetine, paroxetine, sertraline, allergies, e.g., loratidine, and psychosis, e.g., olanzapine.

In particular, the medicament carrier is suitable for containing medicament for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy)propyl]sulfonyl]ethyl]amino]ethyl-2(3H)-benzothiazolone; diuretics, e.g., amiloride; anticholinergics, e.g., ipratropium, tiotropium, atropine or oxitropium; hormones, e.g., cortisone, hydrocortisone or prednisolone; xathines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, ipratropium bromide, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). A particularly preferred combination comprises salmeterol xinafoate salt and fluticasone propionate.

It may be appreciated that any of the parts of the medicament carrier which contact the medicament may be coated with materials such as fluoropolymer materials which reduce the tendency of medicament to adhere thereto. Suitable fluoropolymers include polytetrafluoroethylene (PTFE) and fluoroethylene propylene (FEP).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims or may include, by way of example and without limitation, one or more of the following claims.

What is claimed is:

1. A carrier comprising a sheet having a first portion and a second portion; a preformed retainer in said first portion said retainer comprising a pocket or a hole in said first portion; a fold in said second portion such that the second portion is foldable towards the retainer to form a cover for said retainer; and a join between said cover and the retainer, wherein said retainer is present in said first portion and suitable for receipt of product prior to being covered with said second portion, and wherein said retainer is present in said first portion and suitable for containment of a product after said retainer is exposed.

2. A carrier according to claim 1, wherein said sheet comprises an elongate strip.

3. A carrier according to claim 1, wherein said hole additionally comprises a seal applied thereto.

4. A carrier according to claim 1 comprising a plurality of retainers in the first portion, wherein the second portion is foldable towards said plurality of retainers to form a cover therefor; and a join between said cover and the plurality of retainers.

5. A carrier according to claim 1, additionally comprising a fold in said first portion such that the first portion is foldable towards the retainer to form a base therefor; and a join between said base and the retainer.

6. A carrier according to claim 1, additionally comprising an inert support within the retainer for bearing product thereon.

7. A carrier according to claim 1, comprising a second fold in the second portion to form a pull release tab.

8. A carrier according to claim 7, wherein said pull release tab is shaped for ease of grip.

9. A carrier according to claim 7, wherein the pull release tab has a looped end.

10. A carrier according to claim 7, wherein said pull release tab has at least one perforation therein.

11. A method of opening a carrier as claimed in claim 7 comprising pulling the pull release tab in order to enable access to the retainer.

12. A carrier in multi-unit form comprising a series arrangement of a plurality of carriers according to any claim 1.

13. A carrier according to claim 12, wherein each of said plurality of carriers is connected together.

14. A carrier according to claim 13, wherein each of the plurality of carriers is formable from the same sheet or elongate strip.

15. A carrier according to claim 14, wherein said sheet or elongate strip has a point of weakness between each carrier in said series arrangement.

16. A carrier according to claim 1, wherein the sheet or elongate strip is flexible.

17. A carrier according to claim 1, wherein the sheet or elongate strip comprises material selected from the group consisting of metal foil, an organic polymeric material and paper.

18. A carrier according to claim 17, wherein the carrier comprises a laminate.

19. A carrier according to claim 1, wherein the join is formable by a joining method selected from the group consisting of heat, laser, radio frequency, adhesive, staple, stamp, pressure and ultrasonic sealing.

20. A carrier according to claim 1, wherein the join is peelable to enable peelable access to the retainer.

21. A carrier according to claim 1, wherein the retainer is shaped for receipt by a holder.

22. A carrier according to claim 1, comprising a medicament therein.

23. A carrier according to claim 22, wherein said medicament is in dry powder, tablet, liquid, paste, cream or capsular form.

24. A carrier according to claim 22, wherein the medicament is selected from the group consisting of albuterol, salmeterol, ipratropium bromide, fluticasone propionate and beclomethasone dipropionate and salts or solvates thereof and any mixtures thereof.

25. A inhalation device comprising a housing in combination with a carrier as claimed in claim 22.

26. An inhalation device according to claim 25, wherein said housing includes a holder for receipt of the retainer of the carrier.

27. An inhalation device according to claim 25, wherein the carrier comprises a pull release tab and the pull release tab protrudes from the housing.

28. An inhalation device according to claim 27, wherein the inhalation device comprises a release mechanism and the pull release tab connects to the release mechanism.

29. An inhalation device according to claim 28, wherein said release mechanism is separable from the housing.

30. A carrier of claim 22 wherein said medicament is used in the treatment of respiratory disorders.

31. A carrier according to claim 30, wherein the medicament is used in the treatment of asthma.

32. A carrier according to claim 31, wherein said medicament comprises a medicament selected from the group consisting albuterol, salmeterol, ipratroprium bromide, fluticasone propionate, and beclomethasone dipropionate, and salts or solvates thereof, and mixtures thereof.

33. A carrier according to claim 1, comprising an electronic component therein.

34. A carrier according to claim 33, wherein said electronic component is selected from the group consisting of semi-conductor, integrated circuit chip, fuse and battery.

35. A carrier according to claim 1, comprising a food therein.

36. A carrier according to claim 35, wherein said food is selected from the group consisting of meat, mycoprotein, milk, cheese, flour, pasta, rice, oil, sugar, confectionery, vegetable, herbal, snack, convenience and fruit foodstuffs.

37. A carrier according to claim 1, comprising a beverage therein.

38. A carrier according to claim 37, wherein said beverage is selected from the group consisting of water, milk, coffee, cocoa, tea, fruit, carbonated and alcoholic drinks.

39. A carrier according to claim 1, comprising a toiletry therein.

40. A carrier according to claim 39, wherein said toiletry is selected from the group consisting of toothpaste, soap, mouthwash, shampoo, skin and face cream.

41. A carrier according to claim 1, comprising a cleanser therein.

42. A carrier according to claim 41, wherein said cleanser is selected from the group consisting of soap, detergent, enzymic preparation and organic solvent.

43. A carrier according claim 1, comprising a disinfectant therein.

44. A carrier according to claim 43, wherein said disinfectant is selected from the group consisting of sterilant, antiseptic and bleach.

45. A carrier according to claim 1, comprising a light-sensitive material therein.

46. A carrier according to claim 45, wherein said light-sensitive material comprises a photographic film.

47. A carrier according to claim 1, comprising a marking material therein.

48. A carrier according to claim 47 wherein said marking material is selected from the group consisting of toner, ink, dye, pigment, acid and alkali.

49. A carrier according to claim 1, comprising a covering material therein.

50. A carrier according to claim 49, wherein said covering material is selected from the group consisting of pains, pigment, dye, corrosion inhibitor, electrical conductor, electrical insulator and static inhibitor.

51. A carrier according to claim 1, comprising a toy therein.

52. A carrier according to claim 51, wherein said toy is selected from the group consisting of model, figure, doll, animal, jigsaw and game.

53. A carrier according to claim 1, comprising haberdashery therein.

54. A carrier according to claim 53, wherein said haberdashery is selected from the group consisting of button, bobbin, needle, pin, eye, hook and fastener.

55. A carrier according to claim 1, comprising a tool therein.

56. A carrier according to claim 55, wherein said tool comprises a domestic tool.

57. A carrier according to claim 56, wherein said domestic tool is selected from the group consisting of can opener, bottle opener, ring-pull opener, scissors, knife, fork and spoon.

58. A carrier according to claim 55, wherein the tool comprises a home maintenance tool.

59. A carrier according to claim 58, wherein said home maintenance tool is selected from the group consisting of nail, screw, pin, wire, screwdriver, knife, brush, spanner, ruler and marker.

60. A carrier according to claim 1, comprising stationery therein.

61. A carrier according to claim 60, wherein said stationery is selected from the group consisting of pencil, pen, ruler, crayon, eraser, marker, stencil, protractor, compass and paper.

62. A carrier according to claim 1, comprising an adhesive therein.

63. A carrier according to claim 62, wherein said adhesive bonds materials selected from the group consisting of paper, plastic, wood, rubber, glass and metal.

64. A carrier according to claim 1, comprising an agrochemical therein.

65. A carrier according to claim 64, wherein said agrochemical is selected from the group consisting of herbicide, insecticide, fungicide, rodentocide, nematocide, acaracide and plant growth regulator.

66. A carrier according to claim 1, comprising a plant seed therein.

67. A carrier according to claim 66, wherein said seed is derived from plants selected from the group consisting of monocotyledonous and dicotyledonous plants.

68. A carrier according to claim 1, comprising a contraceptive therein.

69. A carrier according to claim 68, wherein said contraceptive is either a contraceptive device or a contraceptive drug.

70. A carrier according to claim 69, wherein said contraceptive device is selected from the group consisting of condom, diaphragm, sponge and coil.

71. A carrier according to claim 69, wherein said contraceptive drug is selected from the group consisting of spermacide, estrogen, ethinyl estradiol, progesterone, levonorgestrel and nongestrel.

72. A carrier according to claim 1, comprising a medical instrument therein.

73. A carrier according to claim 72, wherein said medical instrument is selected from the group consisting of scalpel, thermometer and syringe.

74. A carrier according to claim 1, comprising laboratory equipment therein.

75. A carrier according to claim 74, wherein said equipment is selected from the group consisting of dispenser tip, microbial filter, filter paper, aseptic container, petri-plate, vial, test tube, tissue-culture vessel and pipette.

76. A carrier according to claim 1, comprising a catemenial product therein.

77. A carrier according to claim 76, wherein said catemenial product comprises a tampon.

78. A carrier according to claim 1, comprising nicotine therein.

79. A carrier according to claim 22, wherein said medicament comprises albuterol sulfate.

80. A method of making a carrier comprising:
(a) forming a retainer, comprising a pocket or hole in a first portion of a sheet or elongate strip, said first portion defining a lip portion which defines the opening to said retainer said retainer being present in said first portion throughout the useful life of the sheet or elongate strip;
(b) filling said retainer with product;
(c) folding a second portion of said sheet or elongate strip towards the retainer to form a cover therefor; and
(d) forming a join between said cover and the retainer.

81. A method according to claim 80 comprising forming a plurality of retainers in a said portion of said sheet or elongate strip; filling said plurality of retainers with product; folding a second portion of the sheet or elongate strip towards the plurality of retainers to form a cover therefor; and forming a join between said cover and the plurality of retainers.

82. A method of making a carrier in multi-unit form comprising successive iterations of the method according to claim 80 to form a series arrangement of a plurality of carriers.

83. A method of making a carrier according to claim 80, additionally comprising a fold in said first portion such that the first portion is foldable towards the retainer to form a base therefor; and a join between said base and the retainer.

* * * * *

UNITED STATES PATENT AND TRADEMARK OFFICE
CERTIFICATE OF CORRECTION

PATENT NO. : 6,929,004 B1
DATED : August 16, 2005
INVENTOR(S) : Bonney et al.

It is certified that error appears in the above-identified patent and that said Letters Patent is hereby corrected as shown below:

Column 10,
Line 4, "to any claim 1" should read -- to claim 1 --.

Column 11,
Line 39, "pains," should read -- paint, --.

Signed and Sealed this

Eighth Day of November, 2005

JON W. DUDAS
*Director of the United States Patent and Trademark Office*